(12) United States Patent
Kilic et al.

(10) Patent No.: US 11,944,830 B2
(45) Date of Patent: Apr. 2, 2024

(54) FEEDTHROUGH SYSTEM

(71) Applicant: Heraeus Deutschland Gmbh & Co. KG, Hanau (DE)

(72) Inventors: Beytullah Yasin Kilic, Karlstein (DE); Leoni Wilhelm, Hanau (DE); Jakob Fischer, Hanau (DE); Jens Trötzschel, Hanau (DE)

(73) Assignees: Heraeus Deutschland GmbH & Co. KG, Hanau (DE); Heraeus Additive Manufacturing GmbH, Hanau (DE)

( * ) Notice: Subject to any disclaimer, the term of this patent is extended or adjusted under 35 U.S.C. 154(b) by 192 days.

(21) Appl. No.: 17/240,430

(22) Filed: Apr. 26, 2021

(65) Prior Publication Data
US 2021/0330984 A1    Oct. 28, 2021

(30) Foreign Application Priority Data
Apr. 28, 2020    (EP) .................................... 20171929

(51) Int. Cl.
*H01B 17/30*    (2006.01)
*A61N 1/375*    (2006.01)
(Continued)

(52) U.S. Cl.
CPC ......... *A61N 1/3754* (2013.01); *H01B 17/303* (2013.01); *H01R 13/5224* (2013.01); *H01L 23/481* (2013.01); *H01R 2201/12* (2013.01)

(58) Field of Classification Search
USPC ........................................... 29/879; 174/650
See application file for complete search history.

(56) References Cited

U.S. PATENT DOCUMENTS 8,494,635 B2 *  7/2013  Troetzschel ............. H02G 3/02
                                                    607/116
8,929,987 B2 *  1/2015  Troetzschel ......... A61N 1/3754
                                                    607/37
(Continued)

FOREIGN PATENT DOCUMENTS

EP        3228354      10/2017
WO     2013/019458     2/2013
(Continued)

OTHER PUBLICATIONS

Biological Responses to Metal Implants, U.S. Food & Drug Administration, Sep. 2019.
(Continued)

*Primary Examiner* — Krystal Robinson
(74) *Attorney, Agent, or Firm* — Dicke, Billig & Czaja, PLLC (57) ABSTRACT

One aspect is a feedthrough system including a) a feedthrough including i) an insulating body, ii) an electrically conductive pathway, wherein an end of the electrically conductive pathway is level with a surface of the insulating body, iii) an electrically conductive pad, wherein the electrically conductive pad is attached to the level end of the electrically conductive pathway, b) an electrical contact element including a metal, wherein the electrical contact element is attached to the level end of the electrically conductive pathway by a joint microstructure, or wherein, when the feedthrough includes an electrically conductive pad, the electrical contact element is attached to the electrically conductive pad by a joint microstructure. Furthermore, the present embodiment refers to a process for preparing the inventive feedthrough system, and to a device including the inventive feedthrough system.

20 Claims, 4 Drawing Sheets

(51) Int. Cl.
    *H01R 13/52*     (2006.01)
    *H01L 23/48*     (2006.01)

(56) References Cited

U.S. PATENT DOCUMENTS

| | | | | |
|---|---|---|---|---|
| 9,032,614 | B2* | 5/2015 | Specht | H01R 13/5224 |
| | | | | 29/25.42 |
| 9,403,023 | B2* | 8/2016 | Markham | C23C 4/134 |
| 9,431,801 | B2* | 8/2016 | Markham | B23K 1/0056 |
| 9,504,840 | B2 | 11/2016 | Pavlovic et al. | |
| 10,212,836 | B2* | 2/2019 | Dittmer | C25D 7/00 |
| 2011/0270330 | A1* | 11/2011 | Janzig | H01R 43/0221 |
| | | | | 156/60 |
| 2013/0138186 | A1* | 5/2013 | Iyer | A61N 1/05 |
| | | | | 607/116 |
| 2017/0291033 | A1* | 10/2017 | Dittmer | B23K 11/002 |
| 2018/0213665 | A1 | 7/2018 | Dittmer et al. | |
| 2019/0201699 | A1* | 7/2019 | Dittmer | A61N 1/3754 |

FOREIGN PATENT DOCUMENTS

| | | |
|---|---|---|
| WO | 2016/0145029 | 9/2016 |
| WO | 2016/187365 | 11/2016 |

OTHER PUBLICATIONS

Barlow, Fred D. III, "Ceramic Interconnect Technology Handbook", CRC Press, 2007.

\* cited by examiner

FEEDTHROUGH SYSTEM

CROSS-REFERENCE TO RELATED APPLICATION

This Utility Patent application claims priority to European Application No. 20 171 929.1 filed on Apr. 28, 2020, which is incorporated herein by reference.

TECHNICAL FIELD

The present embodiments relate to a feedthrough system, a process for preparing the feedthrough system, and a device including the feedthrough system.

BACKGROUND

A feedthrough includes an insulating body and an electrical conductor extending through the insulating body. A feedthrough establishes an electrical connection between the interior space and the exterior space of a grounded device. Feedthroughs are extensively used in electronic devices. For example, feedthroughs are used in implantable medical devices, where they electrically connect the hermetically sealed interior space of the device with the exterior bodily fluid side of the device.

In a conventional feedthrough system, a wire or a wire pin is brazed into a metallized ceramic insulator, which, in turn, is likewise brazed into a metal frame, the so-called ferrule. The feedthrough system may then be inserted into the metal housing of a device such as a medical device by a welding step. Such conventional feedthrough systems have certain disadvantages. The assembly of the system requires many steps, a plethora of single parts, and a lot of labor and cost. Due to the many different pieces and their potential failure modes, a microelectronic device or medical device can usually include only a certain number of such conventional feedthroughs, which limits its application. Furthermore, the design of conventional feedthroughs is usually restricted to a wire or wire pin, which has a circular cross section and extends straight through the insulating body.

As an alternative to the conventional pin-based feedthrough, feedthroughs are available which directly integrate the electrical conductor into the insulating body. Such feedthroughs may be prepared by a high-temperature co-fired ceramic (HTCC) process or a low-temperature co-fired ceramic (LTCC) process.

In an exemplary HTCC process, a flexible ceramic green tape is made in a first step using tape casting. The ceramic green tape may be based on alumina and may contain organic additives. In a next step, holes are punched into the green tape. The holes in the green tape are subsequently filled by an electrically conductive paste such as a metal paste or a cermet paste. The conductive paste may be filled into the holes by a stencil printing step. Many of such filed green tapes may then be assembled in form of a multi-layer body and co-fired at high temperatures. The result is a dense, one-piece feedthrough including an insulating body with embedded electrically conductive pathways.

Directly embedding the conductor into the insulating body avoids the brazing of a conductor pin into the insulator. This may lead to a more efficient preparation of the feedthrough as less single pieces are needed and less laborious process steps are required. Furthermore, it is possible to increase the number of conductors in a feedthrough system, which broadens its applicability e.g. in microelectronic or medical devices. Usually, the end of the conductor forms a common and flush surface with the insulator surface, allowing for a further miniaturization of the device. The direct integration of the conductor into the insulator may also provide for a hermetic seal between the conducting element and the insulator, and therefore may contribute to a hermetic seal between the inner space and the outer space of a device. A hermetically sealed device is of greatest importance e.g. in implantable medical devices.

However, the direct integration of electrical conductors into the insulator also poses certain challenges. For example, attaching a connecting wire to an end of the electrically conductive pathway in a reliable manner has proven to be difficult. This is even more the case if the end of the electrically conductive pathway is level with the surface of the insulator. A weak connection between a wire and the conductor of the feedthrough may ultimately lead to a failure of the connection, and thus to a failure of the device. Such a failure can have dramatic consequences, especially in case an implantable medical device.

In view of the above, there is a need in the art for improved, or at least alternative, feedthrough systems. In particular, it is desirable that the feedthrough system is a one-piece feedthrough system, which allows for improving the attachment of a connecting wire to the end of the electrical conducting element of the feedthrough.

It is one object of one embodiment to provide an improved, or at least alternative, feedthrough system, an improved, or at least alternative process for preparing a feedthrough system, and/or an improved, or at least alternative, device including a feedthrough system.

SUMMARY

The object of one embodiment has been achieved by the feedthrough system as defined in the independent claims.

One aspect of one embodiment refers to a feedthrough system including
  a) a feedthrough including
    i) an insulating body,
    ii) an electrically conductive pathway, wherein an end of the electrically conductive pathway is level with a surface of the insulating body,
    iii) optionally a electrically conductive pad, wherein the electrically conductive pad is attached to the level end of the electrically conductive pathway,
  b) an electrical contact element including a metal, wherein the electrical contact element is attached to the level end of the electrically conductive pathway by a joint microstructure, or
  wherein, when the feedthrough includes a electrically conductive pad, the electrical contact element is attached to the electrically conductive pad by a joint microstructure.

By attaching an electrical contact element to the level end of an electrically conductive pathway, it is possible to reliably connect a wire to the feedthrough e.g. by brazing, soldering or melting the wire to the contact element. The electrical contact element is attached to the level end of the conductor by a joint microstructure, which renders a delamination of the contact element impossible, or at least significantly less likely. The presence of the contact element places the point for attaching the wire to the feedthrough remote from the insulating body and the conductive pathway. Thereby, the insulating body or the conductive pathway is less likely to be microfractured when the wire is attached to the feedthrough e.g. by a brazing step. In view of the foregoing, the inventive feedthrough system has a higher quality, especially in terms of robustness, than comparable known feedthroughs. The inventive feedthrough system may be prepared in an easy and effective manner.

The same effect is obtained in case an electrically conductive pad is attached to the level end of the conductive pathway, wherein the electrically conductive pad is then attached to the electrical contact element by a joint microstructure. Furthermore, the presence of the electrically conductive pad in combination with the contact element places the point for attaching the wire to the feedthrough even more remote from the insulating body and the conductive pathway. Thereby, the insulating body or the conductive pathway is even less likely to be microfractured when the wire is attached to the feedthrough e.g. by a brazing step.

One aspect of one embodiment relates to a process for preparing a feedthrough system according to the present embodiments including the steps of:

1) providing a feedthrough including
   i) an insulating body,
   ii) an electrically conductive pathway, wherein an end of the electrically conductive pathway is level with a surface of the insulating body, and
   iii) optionally an electrically conductive pad, wherein the electrically conductive pad is attached to the level end of the electrically conductive pathway,
2) depositing a metal onto the level end of the electrically conductive pathway by a metal additive manufacturing process to obtain an electrical contact element, wherein the electrical contact element is attached to the level end of the electrically conductive feedthrough by a joint microstructure, or when the feedthrough includes an electrically conductive pad, depositing a metal onto the electrically conductive pad by a metal additive manufacturing process to obtain an electrical contact element, wherein the electrical contact element is attached to the electrically conductive pad by a joint microstructure.

One aspect of one embodiment refers to a device including the feedthrough system according to the present embodiments.

Preferred embodiments are defined in the dependent claims.

It should be understood that for the purposes of the present embodiments, the following terms have the following meanings:

An "electrically conductive pathway" means an electrically conductive element, which extends from a first surface of the insulating body (e.g. an interior surface) to a second surface of the insulating body (e.g. an exterior), and which allows for conducting an electrical signal from an interior space through the insulating body to an exterior space.

A "surface" of the insulating body means a surface of the insulating body, which is in contact with the space surrounding the feedthrough system or the device, i.e. is not attached to another component of the feedthrough system, or of the device.

"The end is level with a surface" means that the end of the electrically conductive pathway extending through the insulating body is at the same level, or at a similar level, as a surfaces of the insulating body. For example, an end of the conductive pathway may be at the same level as the surface of the insulating body, or may have a distance to the level of a surface of the insulating body, which is below 2 mm, preferably below 1 mm, more preferably below 500 µm, even more preferably below 100 µm, and most preferably below 50 µm.

The "level end" of the electrically conductive pathway refers to the at least one end of the electrically conductive pathway which is level with a surface of the insulating body.

A "joint microstructure" refers to a part of the electrical contact element, which is molten with a part of the level end of the conductive pathway, or with a part of the electrically conductive pad, thereby forming a cohesive bond between the parts.

The term "metal" is meant to encompass metals in their elemental form, and mixtures or alloys of metals.

Where an indefinite or definite article is used when referring to a singular noun, e.g., "a", "an" or "the", this includes a plural of that noun unless anything else is specifically stated.

Where the term "comprising" is used in the present description and claims, it does not exclude other elements. For the purposes of the present embodiments, the term "consisting of" is considered to be a preferred embodiment of the term "comprising". If hereinafter a group is defined to comprise at least a certain number of embodiments, this is also to be understood to disclose a group, which preferably consists only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

BRIEF DESCRIPTION OF THE DRAWINGS

The following schematic drawings show aspects of the embodiments for improving the understanding of the embodiments in connection with some exemplary illustrations, wherein.

DETAILED DESCRIPTION

In the following the present embodiments will be set out in more detail:

The feedthrough system according to the present embodiments include a feedthrough.

The feedthrough includes an insulating body.

The insulating body may be any type of insulating body suitable for being used in a feedthrough, preferably in a feedthrough of an implantable medical device.

The insulating body may be a ceramic insulating body. The ceramic insulting body may be an oxide ceramic, a silicate ceramic and a non-oxide ceramic or a combination of at least two thereof.

The oxide ceramic may comprise a metal oxide or a metalloid oxide or both. The metal of the metal oxide may be selected from the group consisting of aluminum, zirconium, titanium, or a combination of at least two thereof. For example, the metal oxide may be selected from the group consisting of aluminium oxide ($Al_2O_3$); magnesium oxide (MgO); zirconium oxide ($ZrO_2$); yttrium oxide ($Y_2O_3$); aluminium titanate ($Al_2TiO_5$); a piezo ceramic as for example lead-zirconate ($PbZrO_3$), lead-titanate ($PbTiO_3$) and lead-circonate-titanate (PZT); or a combination of at least two thereof. A metalloid of the metalloid oxide may be selected from the group consisting of boron, silicon, tellurium, or a combination of at least two thereof.

The silicate ceramic may be selected from the group consisting of a steatite ($Mg_3[Si_4O_{10}(OH)_2]$), a cordierite ($Mg, Fe^{2+})_2(Al_2Si)[Al_2Si_4O_{18}]$), a mullite, a feldspar ($Ba, Ca, Na, K, NH_4)(Al, B, Si)_4O_8$) or a combination of at least two thereof.

The non-oxide ceramic may comprise a carbide or a nitride or both. For example, the carbide may be one selected from the group consisting of silicon carbide (SiC), boron carbide ($B_4C$), titanium carbide (TiC), tungsten carbide, cementite ($Fe_3C$) or a combination of at least two thereof. The nitride may be one selected from the group consisting of silicon nitride ($Si_3N_4$), aluminium nitride (AlN), titanium nitride (TiN), silicon aluminium oxinitride (SIALON) or a combination of at least two thereof.

It is preferred in one embodiment that the insulating body is an oxide ceramic including a metal oxide. Preferably, the metal oxide is aluminum oxide ($Al_2O_3$). A suitable aluminum oxide is one having a high purity, e.g. ≥98 wt. %, based on the total weight of the aluminum oxide.

It is preferred in one embodiment that the insulating body is a multi-layer ceramic body. Multi-layer ceramic bodies are known to the skilled person. Multi-layer ceramic bodies may be obtained by firing or sintering an assembly of ceramic green tapes. Such processes are well-known to the skilled artisan. It is also referred to the description of the inventive process below.

In one embodiment, the insulating body of the feedthrough is a multi-layer ceramic including aluminum oxide.

The insulating body includes a first surface and a second surface. Preferably, the first surface is suitable as an exterior surface of an implantable medical device and the second surface is suitable as an interior surface of an implantable medical device.

The geometry of the insulating body is not limited as long as the geometry allows for the use of the insulating body in a feedthrough for a device, preferably for an implantable medical device. The insulating body may have a rectangular, a box-shaped or a cylindrical form. Preferably, the insulating body has a geometric form, which allows for inserting the insulating body into a housing of a device, preferably of an implantable medical device.

The dimensions of the insulating body are not particularly limited. It is preferred that the insulating body has dimensions which make it suitable for being used in a microelectronic device or implantable medical device.

For example, the insulating body may have width in the range of 1 mm to 10 cm, preferably in the range of 1 mm to 5 cm, more preferably in the range of 2 mm to 2 cm, and/or the insulating body may have a height in the range of 100 µm to 10 cm, preferably in the range of 200 µm to 5 cm, more preferably in the range of 500 µm to 1 cm, and/or the insulating body may have a length in the range of 1 mm to 10 cm, preferably in the range of 1 mm to 5 cm, more preferably in the range of 2 mm to 2 cm.

For example, the insulating body may have a width of 6 mm, a height of 1 mm, and a length of 16 mm.

The feedthrough further includes an electrically conductive pathway, wherein an end of the electrically conductive pathway is level with a surface of the insulating body.

The level end of the electrically conductive pathway may be at the same plane as a surface of the insulating body. The level end of the electrically conductive pathway may be flush with a surface of the insulating body. However, the level end of the electrically may also project beyond the surface (e.g. into the space beyond the surface of the body, or into the internal space of the body) as long as it is still considered a level end in the meaning of the above definition.

Preferably, the electrically conductive pathway has a first end being level with a first surface of the insulating body, and a second end being level with a second surface of the insulating body. However, it is also possible that a first end of the pathway is level with a first surface of the insulating body, while a second end of the pathway projects beyond a second surface of the insulating body, for example into the external space or into the internal space of the insulating body.

The electrically conductive pathway has at least a first end and a second end allowing the conduction of an electrical signal through the insulating body. However, the electrically conductive pathway mal also have more than two ends. For example, the pathway may have at least one branching. In such case, the conductive pathway may have at least three ends, of which each one may be connected to a surface of the insulating body as described herein.

The electrically conductive pathway may be any type of electrically conductive pathway, which may be integrated into an insulating body so that one end of the pathway is level with a surface of the insulating body. For example, the electrically conductive pathway may be a metal, a metal alloy, or a cermet. A "cermet" in the meaning of the present embodiments is a composite including a metal and a ceramic component.

Preferably in one embodiment, the electrically conductive pathway is a cermet pathway. The use of a cermet as the electrically conductive pathway has the advantage that an interpenetrating network structure may be formed between the insulating body, preferably a ceramic, and the conductive path, for example, in a co-sintering process (e.g. a HTCC process). In other words, there is no clear-cut interface between the insulator and the cermet path. This specific network structure hermetically seals the insulator (e.g. ceramic) with the conductive path in a specifically effective manner. The use of a cermet is further advantageous in that a cermet and the insulating body (e.g. ceramic) have less of a difference in thermal expansion than e.g. a pure metal or a metal alloy and the insulator. In view of the foregoing, the use of a cermet pathway as the electrically conductive pathway of the inventive feedthrough system results in a specifically robust feedthrough system, which can provide for a high hermetic sealing, and which can be prepared in a very efficient manner.

The cermet pathway includes a metal and a ceramic component.

The metal may be a biocompatible metal. "Biocompatible metals" are known to the skilled person. Biocompatible metals are, for example, listed in Appendix B of the publication "Biological Responses to Metal Implants", September 2019, by the FDA.

The cermet pathway in one embodiment includes a metal selected from the group consisting of platinum, gold, iridium, niobium, molybdenum, titanium, cobalt, zirconium, chromium, tantalum, tungsten, and alloys of each one of these metals. Preferably in one embodiment, the cermet pathway includes platinum or a platinum alloy.

The ceramic component is in one embodiment selected from the group consisting of aluminum oxide, magnesium oxide, silicon oxide, zirconium dioxide, zirconium oxide-toughened aluminum oxide, yttrium-toughened zirconium oxide, aluminum nitride, piezoceramic materials, barium(Zr, Ti) oxide, barium(CE, Ti) oxide, and sodium-potassium-niobate. Preferably in one embodiment, the cermet pathway includes aluminum oxide (e.g. alumina oxide with a purity of ≥98 wt. %). In case the insulating body is a ceramic, it is preferred that the cermet includes, or consists of, the same ceramic material.

A cermet becomes electrically conductive if the metal content of the cermet is above the so called percolation threshold, at which metal particles in the sintered cermet are at least partly connected to each other in such a way that electrical charges can be transported via conduction. A skilled person can select the appropriate amount of metal in the cermet, so that the percolation threshold is exceeded. For example, the metal content of the cermet may be, depending on the choice of materials, at least 25 vol.-% (e.g. 25 to 90 vol.-%), preferably at least 50 vol.-% (e.g. 50 to 90 vol.-%), most preferably at least 60 vol.-% (e.g. 38 to 90 vol.-%), each based on the total volume of the cermet. A preferred cermet is characterized by a high specific conductivity, which is preferably at least 1 S/m, more preferably at least 103 S/m, more preferably at least 104 S/m.

The geometry of the electrically conductive pathway is not particularly limited and may be selected by a skilled person according to the needs. For example, the electrically conductive pathway may be cylindrical in shape. However, the pathway may also have more complex geometries extending through the insulting body. Especially, when the electrically conductive pathway is prepared as part of a co-sintering process (e.g. a HTCC process), the geometry of the pathway may be selected by a skilled person as desired.

As it is the case for the insulating body, the dimension of the electrically conductive pathway may be selected to be suitable for a specific device such as a microelectronic device or an implantable medical device. The dimension of the electrically conductive pathway may vary depending on the dimensions of the insulating body. The minimum height of the electrically conductive pathway is predetermined by the insulating body, since the pathway has to extend through the insulating body.

The electrically conductive pathway may have a diameter in the range of from 10 μm to 10 mm, preferably of from 100 μm to 5 mm, more preferably from 200 μm to 1 mm. For example, the electrically conductive pathway may have a diameter of 300 μm.

Preferably, the feedthrough of the inventive feedthrough system is a one-piece feedthrough. A "one-piece" feedthrough means that the feedthrough is directly obtainable as a single piece, e.g. by a co-sintering process. For example, in a one-piece feedthrough the electrically conductive path does not need to be brazed or soldered into the insulating body to obtain the feedthrough.

It is further preferred in one embodiment that the feedthrough, and preferably the feedthrough system, is a hermetically sealed material. In this context, the term "hermetically sealed" means that moisture and/or gases cannot permeate through the hermetically sealed feedthrough, preferably the feedthrough system, at all or only to a minimal extent upon an intended use for a period of time of at least 5 years, preferably in a range of 5 to 10 years. The so-called leak rate, which can be determined, for example, by leak tests, is a physical parameter that can describe, for example, a permeation of gases and/or moisture through a material or a device, for example, through the feedthrough, the inventive feedthrough system or the inventive device. Pertinent leak tests can be carried out with helium leak testers and/or mass spectrometers and are specified in the Mil-STD-883G Method 1014 standard. For example, the feedthrough, the inventive feedthrough system or the inventive device may have a helium leak rate of less than $1\times10^{-7}$ atm*cm$^3$/sec. In one embodiment, the helium leak rate can be less than $1\times10^{-8}$ atm*cm3/sec, in one embodiment, less than $1\times10^{-9}$ atm*cm$^3$/sec. In terms of standardizing, the helium leak rates may be converted into the equivalent standard air leak rates. The definition of the equivalent standard air leak rate and the method of conversion are given in the standard ISO 3530.

It is to be understood that the feedthrough is not limited to a single electrically conductive pathway. The feedthrough may comprise two, three, four or more electrically conductive pathways as described herein. The number of electrically conductive pathways is not specifically limited. It is even possible to include more than 50, or more than 100 electrically conductive pathways into the feedthrough. This may be done, for example, by using a co-sintering process (e.g. a HTCC process) for preparing the feedthrough.

The feedthrough of the inventive feedthrough system optionally includes an electrically conductive pad, wherein the electrically conductive pad is attached to the level end of the electrically conductive pathway. Thus, according to one embodiment, the feedthrough of the inventive feedthrough system includes an electrically conductive pad, wherein the electrically conductive pad is attached to the level end of the electrically conductive pathway.

The electrically conductive pad may be a cermet pad or a metal pad. The electrically conductive pad may be attached to the level end of the electrically conductive pathway by screen printing the pad onto the level end of the electrically conductive pathway of the feedthrough. Alternatively, the electrically conductive pad may be attached to the level end of the electrically conductive pathway by a co-sintering step, in which a pre-cursor of the conductive pad is co-sintered with a precursor of the feedthrough.

According to one embodiment, the electrically conductive pad is a cermet pad. The cermet pad may comprise, or consist of, a metal and a ceramic component, which are selected from the same materials as described above for the cermet pathway. Preferably, the electrically conductive pad is a cermet pad and the electrically conductive pathway is a cermet pathway, wherein the cermet pad and the electrically conductive pathway comprise, preferably consist of, the same materials. In case the cermet pad and the cermet pathway comprise, or consist of the same materials, the cermet pad and the cermet pathway may form a single component.

Alternatively, the electrically conductive pad may be a metal pad. Preferably in one embodiment, the metal pad includes a metal selected from the metals as described below for the electrical contact element. For example, the metal pad may comprise, preferably consist of, platinum or a platinum-iridium alloy. More preferably, the metal pad and the contact element comprise the same metal.

The electrically conductive pad may also comprise more than one component. For example, the electrically conductive pad may have a first component being a cermet pad, and a second component being a metal pad. According to a one embodiment, the electrically conductive pad has a first component being a cermet pad, and a second component being a metal pad, wherein the first component is attached to the electrically conductive pathway, preferably a cermet pathway, and wherein at least the second component is attached to the electrical contact element.

The electrically conductive pad may have specific dimensions.

For example, the electrically conductive pad may have a width in the range of 10 μm to 10 mm, preferably in the range of 100 μm to 5 mm, more preferably in the range of 200 μm to 1 mm, and/or the electrically conductive pad may have a height in the range of 10 μm to 1 mm, preferably in the range of 10 μm to 500 μm, more preferably in the range of 10 μm to 200 μm, and/or the electrically conductive pad may have a length in the range of 10 μm to 10 mm, preferably in the range of 100 μm to 5 mm, more preferably in the range of 200 μm to 1 mm.

The feedthrough system according to one embodiment includes an electrical contact element including a metal, wherein the electrical contact element is attached to the level end of the electrically conductive pathway by a joint microstructure, or wherein, when the feedthrough includes an electrically conductive pad, the electrical contact element is attached at least to the electrically conductive pad by a joint microstructure.

According to one embodiment, the feedthrough system includes an electrical contact element including a metal, wherein the electrical contact element is attached to the level end of the electrically conductive pathway by a joint microstructure.

According to another embodiment, the feedthrough system includes an electrical contact element including a metal, wherein the electrical contact element is attached at least to the electrically conductive pad by a joint microstructure.

It is preferred that the electrical contact element is attached to the level end of the electrically conductive path of the feedthrough, i.e. it is preferred that the feedthrough does not comprise an electrically conductive pad to which the electrical contact element is attached.

It is further to be understood that the feedthrough may comprise as many electrically conductive pads as described above as the feedthrough contains electrically conductive pathways as described herein. Of course, it is also possible that one electrically conductive pad may be attached to a first level end of the conductive pathway, and another electrically conductive pad may be attached to a second level end of the conductive pathway.

It is further to be understood that the following description of the electrical contact element is not restricted to the option wherein the contact element is attached to the conductive pathway or to the option wherein the contact element is attached to the conductive pad. In both options, the electrical contact element may have the properties as described below.

The electrical contact element includes a metal. The metal is not restricted to a specific metal as long as the metal is suitable for the desired application (e.g. attaching a connecting wire) or suitable for being used in the desired device (e.g. an implantable medical device).

Preferably, the metal is a biocompatible metal. For example, the metal may be a metal selected from the group consisting of platinum, gold, iridium, steel, titanium, hafnium, niobium, tantalum, cobalt, chromium, zirconium, rhenium, tungsten, molybdenum, and alloys of each one of these metals, and mixtures thereof. Particularly preferred metals are platinum and platinum/iridium alloys. The platinum/iridium alloy may be a Pt90/Ir10 or a Pt70/Ir30 alloy. Such Pt/Ir alloys are known in the art.

The electrical content element may comprise, or consist of, one metal or one metal alloy. In such case, the electrical contact element consists of a single component. Preferably, the metal of the single component may be matched with the metal of the conductive pathway (or the conductive pad) of the feedthrough. For example, the conductive pathway (or the conductive pad) may comprise platinum, and the electrical contact element may comprise, or consist of, platinum. Matching the metals can improve the attachment of the conductive pathway (or conductive pad) to the contact element.

However, it is also possible that the electrical contact element includes two or more components. For example, the electrical contact element may comprise, preferably consist of, a first component and a second component. The first component may consist of a first metal, and the second component may consist of a second metal, which is different to the first metal. The first component and the second component may be attached to each other, preferably are molten together.

It's also possible that the electrical contact element includes, or consists of, three metallic components, wherein the first metallic component is attached to the electrically conductive pathway (or electrically conductive pad), the second metallic component is attached to the first metallic component and to the third metallic component, and the third metallic component forms a contact area for attaching a wire lead.

Therefore, according to one embodiment, the electrical contact element includes, preferably consists of, two, three, or more components, wherein each one of the components includes, preferably consists of, a metal. The metal of each one of the components is preferably different to the other components of the electrical contact element. For example, the electrical contact element may consist of three components, wherein the first component consists of a first metal (e.g. platinum), the second component consists of another metal (e.g. steel), and the third component consists of yet another metal (e.g. platinum/iridium alloy).

The use of an electrical contact element having two (or more) components has the advantage that the first metal component can be matched with the metal of the electrically conductive pathway (or the metal of the optional conductive pad), and the second (or third) metal component can be matched (e.g. in terms of its thermal expansion) with a connecting wire being attached to the electrical contact element. The matching of the components has the advantages that the attachment of the electrical contact element to the feedthrough and to the connecting wire can be improved (e.g. in case the feedthrough includes a different metal than the wire). The matching of the different metallic components may also have the advantages that less or no fractures are formed in the feedthrough system or other parts of the device, when a wire is attached to the electrical contact element e.g. by a melting process. Also, the use of more than one component (e.g. three components) may allow for preparing a part of the electrical contact element from a comparatively cheap metal (e.g. steel), while still being able to provide other parts of the contact element with the desired functionality.

According to one embodiment, the electrical contact element includes, preferably consists of, a first component consisting of a first metal, preferably platinum, and second component consisting of a second metal being different to the first metal, preferably a platinum/iridium alloy, wherein the first component is attached to the electrically conductive feedthrough, and wherein the second component is attached to, preferably molten to, the first component.

The electrical contact element may be non-porous or may be porous.

The dimensions and the three dimensional design of the electrical contact element is not limited in a specific way. The electrical contact element can have a comparatively simple design in form of e.g. rectangular shape, a box shape, or a cylindrical shape. However, the electrical contact element may also have a more complex design in form of e.g. a hollow body. For example, the electrical contact element may have any design, which can be realized and/or prepared by the use of a metal additive manufacturing process.

According to one embodiment, the electrical contact element has the three dimensional form of a hollow body, preferably the form of a blind hole or a through hole. The hollow body may be designed to fit a connecting wire (e.g. a connecting wire for an implantable medical device) into the inner space of the hollow body. According to one embodiment, the electrical contact element has a three dimensional form, which is suitable for mechanically connecting a wire.

Such a three dimensional form of the contact element has the advantage that e.g. a wire lead can be attached more effectively to the contact element. More precisely, the contact element having the three dimensional form of a hollow body may serve as a connecting socket for a wire.

It is also possible that the inner surface of the hollow body is modified in a specific way. According to one embodiment, the hollow body includes on its inner surface a fixing element. For example, the hollow body of the electrical contact element may have a fixing element, which is formed to fit a fixing element of a wire.

By including a fixing element on the inner surface of the hollow body, it is possible to mechanically attach a connecting wire to the electrical contact element in an even more effective manner.

It is to be understood that no matter which three dimensional form of the contact element is chosen, the electrical contact element can be made from a single metal component (e.g. platinum) or from two or more components, which each consist of different metals (e.g. platinum for a first component and Pt/Ir for a second component). It is further to be understood that the three dimensional form of the contact element can be independent from the choice of a specific metal for the contact element or the choice of a specific number of components for the contact element. For example, the contact element may be a hollow body in form of a through hole, wherein the hollow body consists in a first part of a first metal component (e.g. platinum) and in a second part of a second metal component (e.g. a Pt/Ir alloy).

The dimensions of the electrical contact element may be selected to be suitable for the desired form of the electrical contact element. Thus, the dimensions of the contact element may be smaller for a simple contact element (e.g. a cylindrical contact element) than for a more complex contact element having a three dimensional form of a hollow body, which is suitable for fitting a wire lead (e.g. a wire of an implantable medical device) into the inner space of the hollow body.

According to one embodiment, the electrical contact element has a height in the range of from 10 µm to 5 mm, preferably of from 20 µm to 2 mm, more preferably from 200 µm to 500 µm, and/or wherein the electrical contact element has a width in the range of from 10 µm to 10 mm, preferably of from 100 µm to 5 mm, more preferably from 200 µm to 1 mm.

The electrical contact element is either attached to the level end of the electrically conductive pathway or to the electrically conductive pad by a joint microstructure.

It is to be understood that the joint microstructure being present in the inventive feedthrough system is different, and clearly distinguishable (e.g. by microscopy), from an attachment of two components (e.g. an attachment of a metal to a cermet) which is obtained by e.g. a chemical vapor disposition process (CVD), a physical vapor disposition process (PVD), and a sputtering process.

The joint microstructure may comprise a metal of the electrically conductive pathway (or of the electrically conductive pad) which is molten with the metal of the electrical contact element, and thereby forms a cohesive bond between the metals. For example, the joint microstructure can comprise a metal of an electrically conductive cermet pathway (or an electrically conductive cermet pad) which is molten with the metal of the electrical contact element. Alternatively, the joint microstructure can comprise a metal of an electrically conductive metal pathway (or an electrically conductive metal pad) which is molten with the metal of the electrical contact element.

According to one preferred embodiment, the joint microstructure includes the metal of an electrically conductive cermet pathway, preferably platinum, which is molten with the metal of the electrical contact element, preferably platinum. According to another preferred embodiment, the joint microstructure includes the metal of an electrically conductive cermet pad, preferably platinum, which is molten with the metal of the electrical contact element, preferably platinum. According to yet another preferred embodiment, the joint microstructure includes the metal of an electrically conductive metal pad, preferably platinum, which is molten with the metal of the electrical contact element, preferably platinum.

The joint microstructure may comprise metal having a specific crystal lattice. For example, the joint microstructure may comprise metal having a space-centered and/or a face-centered crystal lattice. The joint microstructure may comprise metal in an amorphous form, i.e. which does not form a regular crystal structure.

The joint microstructure may have a specific thickness. The "thickness" of the joint microstructure in this context refers to the dimension of the joint microstructure in the direction from the electrically conductive pathway (or the electrically conductive pad) to the electrical contact element. The joint microstructure may have a thickness of at least 5 µm. For example, the thickness may be in the range of 5 to 100 µm, or in the range of 5 to 50 µm.

The joint microstructure may have a specific depth. The "depth" of the joint microstructure in this context refers to the part of the joint microstructure, which is derived from and/or part of the electrically conductive pathway (or the electrically conductive pad). The joint microstructure may have a depth of at least 5 µm. For example, the depth may be in the range of 5 to 50 µm, or in the range of 5 to 30 µm.

The thickness and the depth of the joint microstructure may be determined by microscopy (e.g. SEM).

The joint microstructure between the level end of the electrically conductive pathway (or the electrically conductive pad) and the electrical contact element may be obtained by melting the metal of the electrical contact element to the level end of the electrically conductive pathway (or to the electrically conductive pad).

It is preferred that the joint microstructure is obtained by melting the metal of the electrical contact element to the level end of the electrically conductive pathway (or to the electrically conductive pad) by a metal additive manufacturing process. Preferably, the contact element is obtained by a metal additive manufacturing process. Thus, according to one preferred embodiment, the electrical contact element and the joint microstructure is obtained by a metal additive manufacturing process. Metal additive manufacturing processes are known to the skilled person. It is also referred to the description of step 2) of the inventive process below.

Preferably, the metal additive manufacturing process is a selective laser melting process.

A joint microstructure which is obtained by a metal additive manufacturing process can provide a particularly strong integral bond between the contact element and the conductive pathway (or the conductive pad). Thereby, the risk of delamination of the contact element from the feedthrough is minimized.

Since the electrical contact element may be prepared by an additive manufacturing process (preferably a selective laser melting process), the metal(s) of the contact element, its the different components, and/or its three dimensional structure are not specifically limited. Thus, there is a great variety of options for designing the electrical contact element, while at the same time obtaining a particularly robust attachment of the electrical contact element to the feedthrough via the joint microstructure.

As it is case for the electrically conductive pathways and the electrically conductive pad, the inventive feedthrough system may comprise two, three, four or more electrical contact elements as described herein. The number may be selected depending on the number of electrically conductive pathways in the feedthrough and/or the number of conductive pads in the feedthrough.

The feedthrough system according to one embodiment is not limited to a use in a specific device. However, the inventive feedthrough system is especially useful for power electronic devices, microelectronic devices, telecommunication devices, or medical devices. Preferably, the inventive feedthrough system is a feedthrough system for a medical device, more preferably for an implantable medical device, and most preferably an active implantable medical device (AIMD). Suitable AIMDs are, for example, cardiac pacemakers, cardiac defibrillators, and neurostimulators, cochlea implants, implantable cardioverters, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like.

Another aspect of one embodiment relates to a process for preparing a feedthrough system according to the present embodiments including the steps of:
1) providing a feedthrough including
  i) an insulating body,
  ii) an electrically conductive pathway, wherein an end of the electrically conductive pathway is level with a surface of the insulating body, and
  iii) optionally an electrically conductive pad, wherein the electrically conductive pad is attached to the level end of the electrically conductive pathway
2) depositing a metal onto the level end of the electrically conductive pathway by a metal additive manufacturing process to obtain an electrical contact element, wherein the electrical contact element is attached to the level end of the electrically conductive feedthrough by a joint microstructure, or
when the feedthrough includes an electrically conductive pad, depositing a metal onto the electrically conductive pad by a metal additive manufacturing process to obtain an electrical contact element, wherein the electrical contact element is attached to the electrically conductive pad by a joint microstructure.

In step 1) the feedthrough of the inventive feedthrough system is provided. The feedthrough may be prepared by a sintering process. Thus, step 1) of the inventive process may comprise be sintering process.

A sintering process shall generally be understood to mean a procedure for the manufacture of materials or work-pieces, in which powdered ceramic and/or metallic substances are heated and connected in the process. A sintering process can proceed without applying external pressure onto the substance to be heated or can, for example, proceed under elevated pressure onto the substance to be heated, for example under a pressure of at least 2 bar, in one embodiment higher pressures, for example pressures of at least 10 bar, for example, at least 100 bar, or even at least 1000 bar. Furthermore, the process can proceed, for example, fully or partly, at temperatures below the melting temperature of the powdered materials, for example at temperatures of 700° C. to 1700° C. The process can be implemented, for example, fully, or partly in a tool and/or a mold. Such that a forming step can be associated with the sintering process. Aside from the powdered materials, a starting material for the sintering process can include further materials, for example one or more binding agents and/or one or more solvents. The sintering process can proceed in one or more steps, whereby additional steps can precede the sintering process, for example one or more forming steps and/or one or more debinding steps.

Sintering processes for preparing ceramic bodies, and for preparing ceramic bodies including electrically conductive pathways, are generally known to the skilled person. For example, sintering processes are described in "Ceramic Interconnect Technology Handbook", CRC Press, Boca Raton.

Step 1) of the inventive process may comprise a LTCC process or a HTCC process, preferably a HTCC process. LTCC and HTCC processes are known to the skilled person.

Step 1) of the inventive process may comprise the steps of:
1a) preparing a ceramic green compact, wherein the ceramic green compact includes at least one hole filled with a pre-cursor of an electrically conductive pathway,
1b) co-sintering the ceramic green compact and the pre-cursor of the electrically conductive pathway.

Step 1a) may comprise preparing a ceramic green tape from a starting material including a ceramic powder. The starting material may further comprise an organic binder and/or an organic solvent. Suitable binder and solvents for such a purpose are known to the skilled person. The ceramic green tape may be prepared by compressing the starting material in a mold.

Step 1a) may further comprise punching at least one hole into a ceramic green tape, and subsequently fill the at least one hole with a pre-cursor of an electrically conductive pathway. After filling of the holes, the green tape may be dried. A pre-cursor of an electrically conductive pathway may be a metal paste or a cermet paste. The metal paste may comprise a metal powder, and optionally an organic binder and/or an organic solvent. The cermet paste may comprise a metal powder a ceramic powder, and optionally an organic binder (e.g. cellulose) and/or a solvent (e.g. water). The ceramic powder and/or the metal powder preferably have a median grain size of less than 10 µm, preferably less than 5 µm, particularly preferable less than 3 µm. In some cases the ceramic powder of the cermet has an average particle size of at least 15 µm. Therein, the average grain size is particularly the weight median value $d_{50}$. The $d_{50}$ gives the value, at which 50% of the grains of the ceramic powder and/or the metallic powder are smaller than the $d_{50}$.

Step 1a) may further comprise stacking at least two ceramic green tapes filled with pre-cursors as described above, and optionally laminating the stacked green tapes, e.g. in an isostatic press. Subsequently, the stacked green tapes may be subjected to a debinding step.

Step 1b) may further comprise a step of cutting the co-sintered ceramic and/or a step of finishing the surface of the co-sintered ceramic (e.g. a polishing step).

The optional electrically conductive pad may be attached to the level end of the conductive pathway after preparing the feedthrough including the insulating body and the conductive pathway. For example, the electrically conductive pad may be attached by depositing (e.g. by screen printing) the conductive pad onto the level end of the conductive pathway. Preferably, the conductive pad is attached to the level end of the electrically conductive pathway after the surface of the electrically conductive pathway and the insulating body have been subjected to a surface finishing step (e.g. a polishing step).

Alternatively, the optional electrically conductive pad may be prepared simultaneously with the insulating body and the electrically conductive pathway. For example, a pre-cursor of the conductive pad may be placed on a precursor of the electrically conductive pathway in a green ceramic compact as described above, followed by a sintering step as described above. The pre-cursor of the conductive pad may be a metal paste, a cermet paste or both, depending on the design of the electrically conductive pad.

In step 2) of the inventive a metal is deposited onto the level end of the electrically conductive pathway by a metal additive manufacturing process to obtain an electrical contact element, wherein the electrical contact element is attached to the level end of the electrically conductive feedthrough by a joint microstructure, or when the feedthrough includes an electrically conductive pad, a is deposited metal onto the electrically conductive pad by a metal additive manufacturing process to obtain an electrical contact element, wherein the electrical contact element is attached to the electrically conductive pad by a joint microstructure.

According to one embodiment, step 2) relates to depositing a metal onto the level end of the electrically conductive pathway by a metal additive manufacturing process to obtain an electrical contact element, wherein the electrical contact element is attached to the level end of the electrically conductive feedthrough by a joint microstructure.

According to another embodiment, step 2) relates to depositing a metal onto the electrically conductive pad by a metal additive manufacturing process to obtain an electrical contact element, wherein the electrical contact element is attached to the electrically conductive pad by a joint microstructure.

The metal additive manufacturing process may be selective laser melting process, a selective laser sintering process or a direct energy deposition process, and preferably is a selective laser melting process.

The metal additive manufacturing process may proceed by using a laser of a specific power density to micromelt a metal powder in a layer-by-layer melting process onto the level end of the electrically conductive pathway (or the electrically conductive pad) thereby preparing the electrical contact element and attaching the electrical contact element to the level end of the electrically conductive pathway (or the electrically conductive pad) in one step.

The metal additive manufacturing process is preferably a selective laser melting (SLM) process.

SLM processes are known in the art. The SLM process may proceed as a powder bed fusion process that uses high intensity laser as an energy source to melt and fuse selective regions of metal powder, layer by layer, according to a computer aided design (CAD) data. After CAD data preparation and processing, the SLM process may start with laying a layer of metal powder on the feedthrough as described herein in a building chamber. After the powder is laid, a high energy density laser may be used to melt and fuse the area of the metal powder which is to be attached to the level end of the electrically conductive pathway of the feedthrough, and which shall subsequently form the electrical contact element of the feedthrough system. Once the laser scanning is completed, the building platform may be lowered, a next layer of powder may be deposited on top and the laser may scan a new layer. The process may then be repeated for successive layers of powder until the desired electrical contact element is finished.

Process parameters, such as laser power, scanning speed, hatch spacing, and layer thickness, are adjusted such that a single melt vector can fuse completely with the neighbouring melt vectors and the preceding layer. The selective laser melting process may be carried with a specific laser power and a specific laser (scanning) speed, which results in a specific line-energy ($El=P/Vs=(U*I)/V$). The laser may have a power in the range of 5 to 175 W and/or a speed in the range of 10 mm/s to 3000 mm/s. The line-energy may be in the range of 10 J/m to 400 J/m. The laser may be a pulsed laser.

The electrical contact element may be prepared in the selective laser melting process by fusing at least one metal layer having a height in the range of 10 to 55 µm. The number of metal layers being fused in the process is not specifically limited. For example, 20 or more metal layers may be fused in the selective laser melting process.

Another aspect of one embodiment refers to a device including the feedthrough system of the present embodiments.

The device preferably has a housing. The housing may be of any material suitable for the desired application of the device. For example, the housing may comprise, or consist of a metal. The metal may be a biocompatible metal such as titanium.

The housing of the device preferably has an opening for fitting in the feedthrough system according to the present embodiment. The opening may preferably be equipped with a flange forming a recess about the opening of the flange.

The feedthrough system according to one embodiment may be positioned within the opening of the housing and may be attached to the recess of the flange. The attachment may be a braze joint, e.g. prepared from a gold alloy. The feedthrough system may also be attached to the flange by laser welding.

Alternatively, the opening of the housing may be equipped with a ferrule, to which the inventive feedthrough system may be attached, e.g. by brazing or laser welding. The ferrule may be a frame-like metal ferrule (e.g. a titanium ferrule), which is attached to the opening of the housing.

The device is preferably hermetically sealed. "Hermetically sealed" is to be understood as described above.

The feedthrough system according to one embodiment may comprise at least one electrical contact element on the interior side of the device, on the exterior side of the device, or both. Preferably, the electrical contact element of the feedthrough is at least present on the exterior side of the device.

The device may further comprise a wire lead which is connected to the at least one electrical contact element of the inventive feedthrough. The wire lead may be connected to the electrical contact element by brazing or welding (e.g. laser welding). Alternatively or additionally, the wire lead may be attached to the electrical contact element by a fixing element being present on the electrical contact element and/or being present on the wire lead. For example, in case the electrical contact element is provided in form of a hollow body (e.g. a through hole), the wire lead may be attached to the contact element via a fixing element of the wire lead. Additionally or alternatively, the wire lead may also be attached to a fixing element on the inner surface of the hollow body.

The wire lead may comprise a metallic material out of the group consisting of gold, copper, aluminum, palladium, silver, platinum, a platinum alloy, iridium, niobium, molybdenum, titanium, a titanium alloy, tantalum, a tantalum alloy, tungsten, a tungsten alloy, stainless steel, a cobalt-chromium alloy. In other words, the wire may be made of gold, silver, copper, aluminum, alloyed copper, alloyed gold, alloyed silver, palladium coated copper, gold coated silver; welding between these metallic materials results in the formation of disordered or ordered alloys by using diffusion. The wire may also be made in form of clad wires, which means with a metal A in a core of the wire and a different metal B on a surface of the wire. The wire lead may comprise a biocompatible metal, preferably platinum or platinum/iridium alloy. The metal of the wire lead may advantageously match with the metal of the contact element, or with the metal of a component of the contact element which is attached to the wire lead.

The device may further comprise an electronic device in its interior. The electronic device may be connected to the inventive feedthrough system by at least one wire lead.

The inventive device may be a power electronic device, microelectronic device, telecommunication device, or medical device.

Preferably, the device is a medical device, more preferably for an implantable medical device, and most preferably an active implantable medical device (AIMD). Preferred AIMDs are, for example, cardiac pacemakers, cardiac defibrillators, and neurostimulators, cochlea implants, implantable cardioverters, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like.

The features disclosed in the claims, the specification, and the drawings may be essential for different embodiments of the claimed embodiments, both separately and in any combination with each other.

In the following description, reference is made to the accompanying drawings, which form a part hereof, and in which is shown by way of illustration specific embodiments in which the embodiments may be practiced. It is to be understood that other embodiments may be utilized and structural or logical changes may be made without departing from the scope of the present embodiments. The following description of the drawings, therefore, is not to be taken in a limiting sense, and the scope of the present invention is defined by the appended claims.

Figure 1:
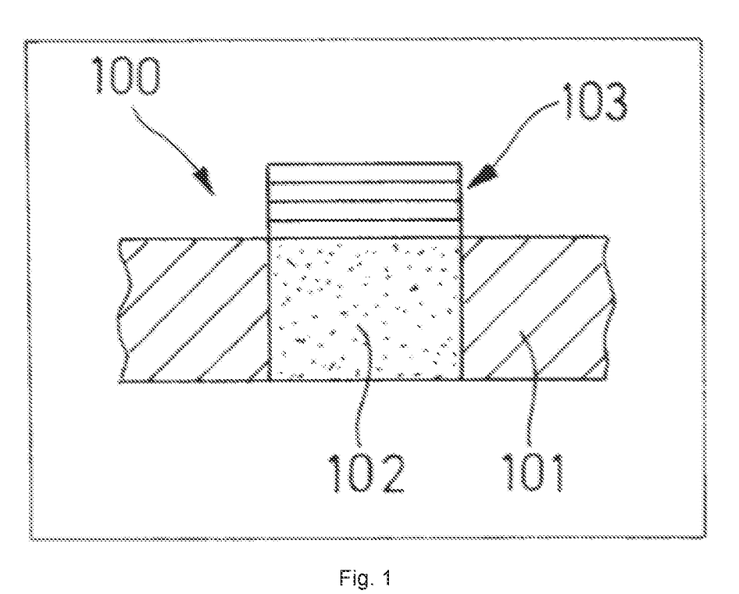
FIG. 1 illustrates a feedthrough system 100 according to one embodiment.

FIG. 1 illustrates a feedthrough system according to one embodiment 100. The feedthrough system includes a feedthrough including an insulating body 101 and an electrically conductive pathway 102. The electrically conductive pathway 102 has a first end being level with a first surface of the insulating body 101 (e.g. the exterior surface of the insulating body) and a second end being level with a second surface of the insulating body 101 (e.g. the interior surface of the insulating body). A contact element 103 including a metal is attached to the first level end of the electrically conductive pathway 102 by a joint microstructure.

According to a preferred embodiment of the inventive feedthrough system 100, the insulating body 101 is a multi-layer ceramic (e.g. including alumina), the electrically conductive pathway 102 is a cermet pathway (e.g. including alumina and platinum) and the contact element 103 includes the same metal as the cermet pathway (e.g. platinum). The contact element 103 may be obtained by a metal additive manufacturing process (e.g. a SLM process).

Figure 2:
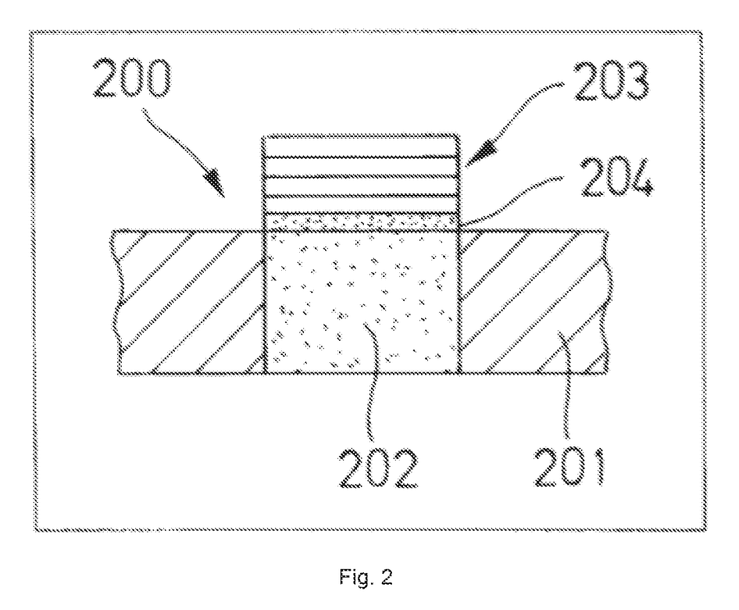
FIG. 2 illustrates a feedthrough system 200 according to one embodiment.

FIG. 2 illustrates a feedthrough system according to one embodiment 200. The feedthrough system includes a feedthrough including an insulating body 201 and an electrically conductive pathway 202. The electrically conductive pathway 202 has a first end being level with a first surface of the insulating body 201 (e.g. the exterior surface of the insulating body) and a second end being level with a second surface of the insulating body 201 (e.g. the interior surface of the insulating body). An electrically conductive pad 204 is attached to the first level end of the electrically conductive pathway 202. A contact element 205 including a metal is attached to the electrically conductive pad 204 by a joint microstructure.

According to a preferred embodiment of the inventive feedthrough system 200, the insulating body 201 is a multi-layer ceramic (e.g. including alumina), the electrically conductive pathway 202 is a cermet pathway (e.g. including alumina and platinum), the electrically conductive pad 204 includes a cermet (e.g. including alumina and platinum), and the contact element 204 includes the same metal as the cermet pad (e.g. platinum). The contact element 203 may be obtained by a metal additive manufacturing process (e.g. a SLM process).

Figure 3:
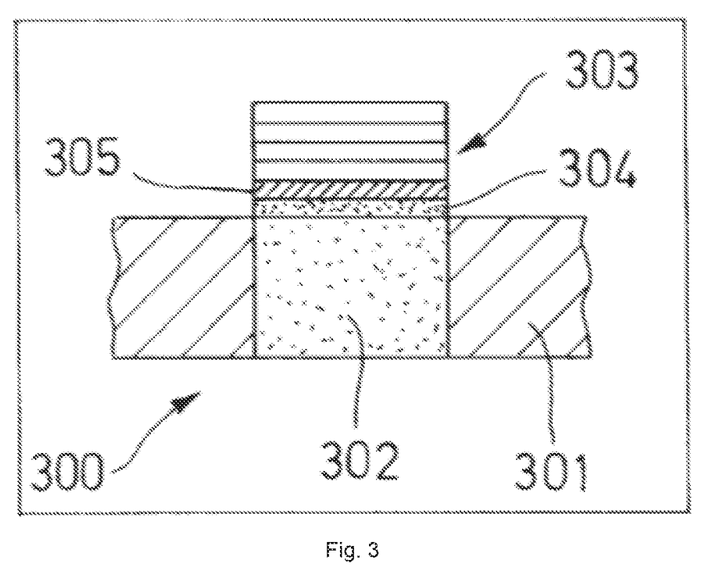
FIG. 3 illustrates a feedthrough system 300 according to one embodiment.

FIG. 3 illustrates a feedthrough system according to one embodiment 300. The feedthrough system includes a feedthrough including an insulating body 301 and an electrically conductive pathway 302. The electrically conductive pathway 302 has a first end being level with a first surface of the insulating body 301 (e.g. the exterior surface of the insulating body) and a second end being level with a second surface of the insulating body 301 (e.g. the interior surface of the insulating body). Feedthrough system 300 further includes an electrically conductive pad consisting of a first component 304 and a second component 305. The first component 304 is attached to the first level end of the electrically conductive pathway 302 and to the second component 305. The second component 305 is attached to an electrical contact element 303 by a joint microstructure.

According to a preferred embodiment of the inventive feedthrough system 300, the insulating body 301 is a multi-layer ceramic (e.g. including alumina), the electrically conductive pathway 302 is a cermet pathway (e.g. including alumina and platinum), the first component 304 of the electrically conductive pad includes a cermet (e.g. including alumina and platinum), the second component 305 of the electrically conductive pad includes, or consists of, a metal (e.g. platinum), and the electrical contact element 303 includes the same metal as the second component 304 of the conductive pad (e.g. platinum). The contact element 303 may be obtained by a metal additive manufacturing process (e.g. a SLM process).

Figure 4:
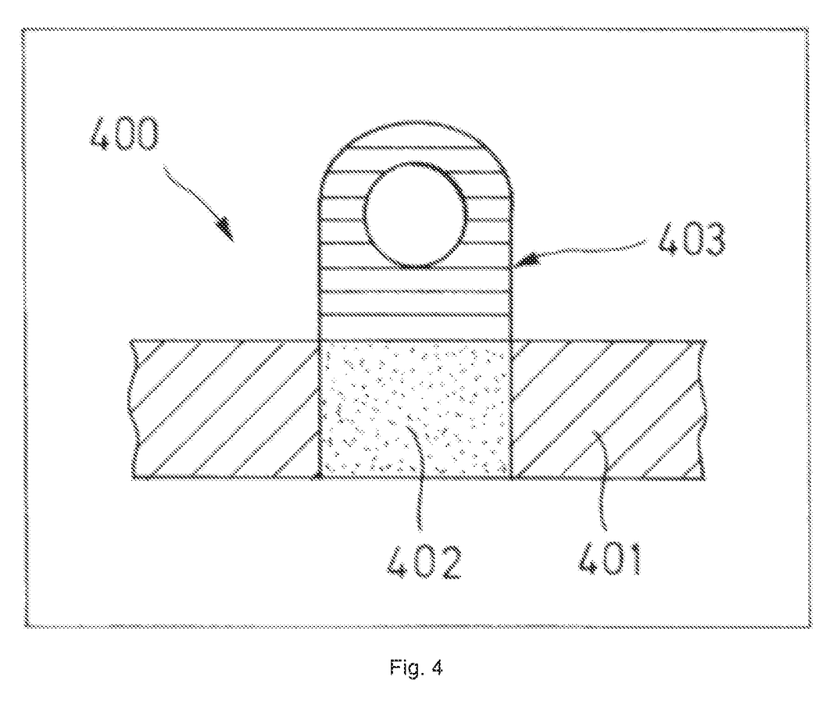
FIG. 4 illustrates a feedthrough system 400 according to one embodiment.

FIG. 4 illustrates a feedthrough system according to one embodiment 400. The feedthrough system includes a feedthrough including an insulating body 401 and an electrically conductive pathway 402. The electrically conductive pathway 402 has a first end being level with a first surface of the insulating body 401 (e.g. the exterior surface of the insulating body) and a second end being level with a second surface of the insulating body 401 (e.g. the interior surface of the insulating body). A contact element 403 including a metal is attached to the first level end of the electrically conductive pathway 402 by a joint microstructure. The contact element 403 includes a through hole.

According to a preferred embodiment of the inventive feedthrough system 400, the insulating body 401 is a multi-layer ceramic (e.g. including alumina), the electrically conductive pathway 402 is a cermet pathway (e.g. including alumina and platinum) and the contact element 403 includes the same metal as the cermet pathway (e.g. platinum). The contact element 403 may be obtained by a metal additive manufacturing process (e.g. a SLM process).

Figure 5:
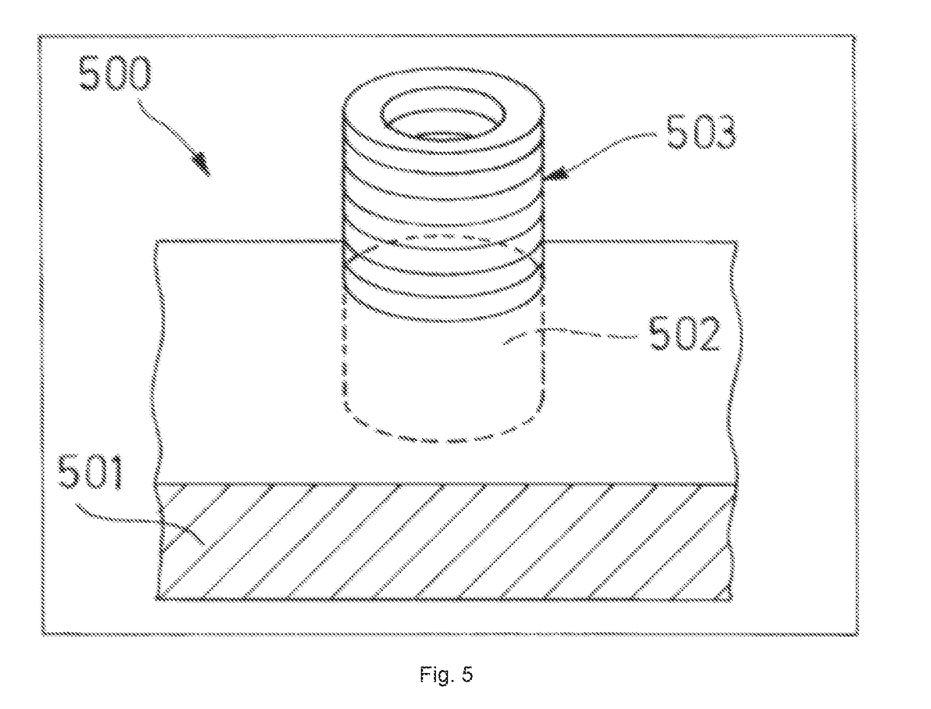
FIG. 5 illustrates a feedthrough system 500 according to one embodiment.

FIG. 5 illustrates a feedthrough system according to one embodiment 500. The feedthrough system includes a feedthrough including an insulating body 501 and an electrically conductive pathway 502. The electrically conductive pathway 502 has a first end being level with a first surface of the insulating body 501 (e.g. the exterior surface of the insulating body). A contact element 503 including a metal is attached to the first level end of the electrically conductive pathway 502 by a joint microstructure. The contact element 503 has the form of a cylinder including a blind hole.

According to a preferred embodiment of the inventive feedthrough system 500, the insulating body 501 is a multi-layer ceramic (e.g. including alumina), the electrically conductive pathway 502 is a cermet pathway (e.g. including alumina and platinum) and the contact element 503 includes the same metal as the cermet pathway (e.g. platinum). The contact element 503 may be obtained by a metal additive manufacturing process (e.g. a SLM process).

Figure 6:
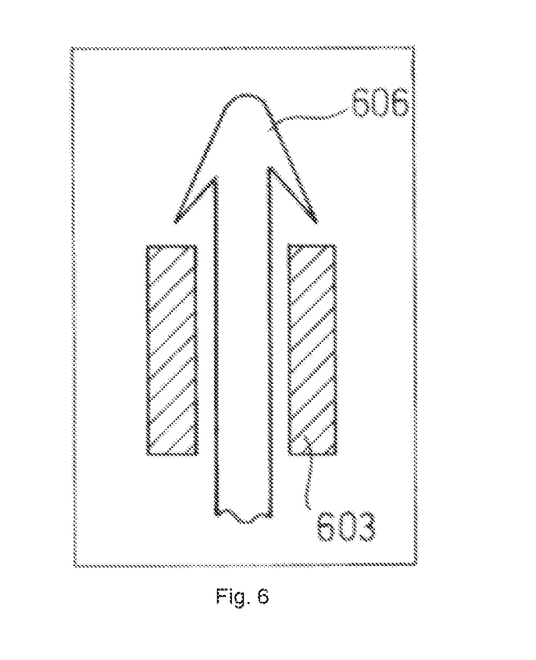
FIG. 6 illustrates a cross section of an electrical contact element 603 of a feedthrough system according to one embodiment, wherein the electrical contact element is in contact with a wire lead 606.

FIG. 6 illustrates a cross section of an electrical contact element 603 being part of an inventive feedthrough system as described herein. The electrical contact element 603 includes a through hole into which a wire lead 606 is inserted. The end of the wire lead 606 includes a fixing element for fixing the wire lead to the electrical contact element 603.

Figure 7:
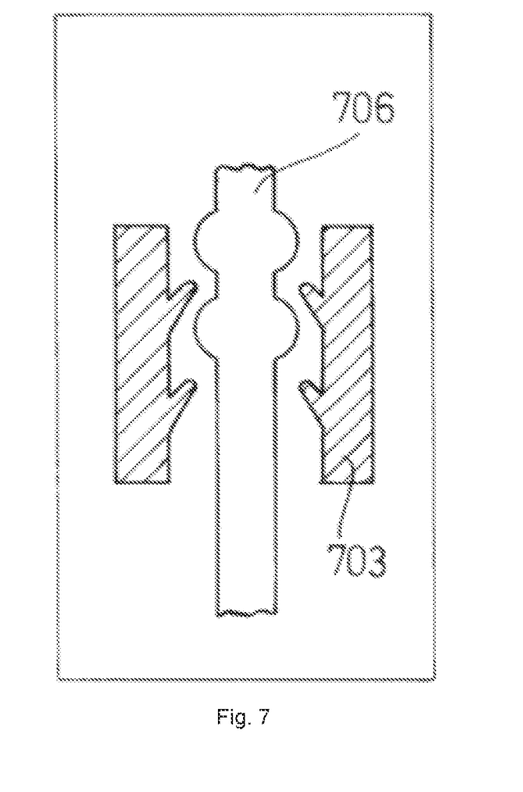
FIG. 7 illustrates a cross section of an electrical contact element 703 of a feedthrough system according to one embodiment, wherein the electrical contact element is in contact with a wire lead 706.

FIG. 7 illustrates a cross section of an electrical contact element 703 being part of an inventive feedthrough system as described herein. The electrical contact element 703 includes a through hole including fixing elements on the inner surface. The electrical contact element 703 is manually attached by its fixing elements to a wire lead 706, which is inserted in the through hole. The wire lead 706 also includes fixing elements, which are shaped to fit with the fixing elements of the electrical contact element 703.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A feedthrough system comprising:
   a) a feedthrough comprising
      i) an insulating body,
      ii) an electrically conductive pathway, wherein an end of the electrically conductive pathway is level with a surface of the insulating body,
   b) an electrical contact element comprising a metal, wherein the electrical contact element is attached to the level end of the electrically conductive pathway by a joint microstructure, and wherein the electrical contact element is configured for connecting a wire to the electrically conductive pathway of the feedthrough.

2. The feedthrough system according to claim 1, wherein the insulating body is a multi-layer ceramic body.

3. The feedthrough system according to claim 1, wherein the electrically conductive pathway is a cermet pathway, and optionally wherein the cermet pathway comprises one or both of:
   (i) a metal selected from the group consisting of platinum, gold, iridium, niobium, molybdenum, titanium, cobalt, zirconium, chromium, tantalum, tungsten, and alloys of each one of these metals, and preferably the metal is platinum or a platinum alloy, and
   (ii) a ceramic component selected from the group consisting of aluminum oxide, magnesium oxide, silicon oxide, zirconium dioxide, zirconium oxide-toughened aluminum oxide, yttrium-toughened zirconium oxide, aluminum nitride, piezoceramic materials, barium(Zr, Ti) oxide, barium(CE, Ti) oxide, and sodium-potassium-niobate, and preferably the ceramic component is aluminum oxide.

4. The feedthrough system according to claim 1, wherein the electrical contact element comprises a biocompatible metal,
   preferably selected from the group consisting of platinum, gold, iridium, steel, titanium, hafnium, niobium, tantalum, cobalt, chromium, zirconium, rhenium, tungsten, molybdenum, and alloys of each one of these metals, and mixtures thereof,
   and more preferably from the group consisting of platinum and platinum/iridium alloys.

5. The feedthrough system according to claim 1, wherein the electrical contact element comprises a first component consisting of a first metal, and second component consisting of a second metal being different to the first metal,
   wherein the first component is attached to attached to the electrically conductive feedthrough, and
   wherein the second component is attached to the first component.

6. The feedthrough system according to claim 1, wherein the electrical contact element has the three dimensional form of a hollow body, preferably the form of a blind hole or a through hole, and optionally wherein the hollow body comprises on its inner surface a fixing element.

7. The feedthrough system according to claim 1, wherein the electrical contact element has a height of in the range of from 10 µm to 5 mm, and optionally wherein the electrical contact element has a width in the range of from 10 µm to 10 mm.

8. The feedthrough system according to claim 1, wherein the electrical contact element and the joint microstructure is obtained by a metal additive manufacturing process, and optionally wherein the metal additive manufacturing process is a selective laser melting process.

9. The feedthrough system according to claim 1, wherein the feedthrough system is a feedthrough system for an implantable medical device.

10. The feedthrough system according to claim 1, wherein the electrical contact element is suitable for connecting a wire to the electrically conductive pathway of the feedthrough by brazing, soldering or melting the wire to the contact element.

11. A feedthrough system comprising:
a) a feedthrough comprising
 i) an insulating body,
 ii) an electrically conductive pathway, wherein an end of the electrically conductive pathway is level with a surface of the insulating body,
 iii) an electrically conductive pad, wherein the electrically conductive pad is attached to the level end of the electrically conductive pathway,
b) an electrical contact element comprising a metal, wherein the electrical contact element is attached to the electrically conductive pad by a joint microstructure, and wherein the electrical contact element is configured for connecting a wire to the electrically conductive pathway of the feedthrough.

12. The feedthrough system according to claim 11, wherein the insulating body is a multi-layer ceramic body.

13. The feedthrough system according to claim 11, wherein the electrically conductive pathway is a cermet pathway, and optionally wherein the cermet pathway comprises one or more of:
(i) a metal selected from the group consisting of platinum, gold, iridium, niobium, molybdenum, titanium, cobalt, zirconium, chromium, tantalum, tungsten, and alloys of each one of these metals, and preferably the metal is platinum or a platinum alloy, and
(ii) a ceramic component selected from the group consisting of aluminum oxide, magnesium oxide, silicon oxide, zirconium dioxide, zirconium oxide-toughened aluminum oxide, yttrium-toughened zirconium oxide, aluminum nitride, piezoceramic materials, barium(Zr, Ti) oxide, barium(CE, Ti) oxide, and sodium-potassium-niobate, and preferably the ceramic component is aluminum oxide.

14. The feedthrough system according to claim 11, wherein the electrical contact element comprises a biocompatible metal,
preferably selected from the group consisting of platinum, gold, iridium, steel, titanium, hafnium, niobium, tantalum, cobalt, chromium, zirconium, rhenium, tungsten, molybdenum, and alloys of each one of these metals, and mixtures thereof,
and more preferably from the group consisting of platinum and platinum/iridium alloys.

15. The feedthrough system according to claim 11, wherein the electrical contact element comprises a first component consisting of a first metal, and second component consisting of a second metal being different to the first metal,
wherein the first component is attached to electrically conductive pad, and
wherein the second component is attached to the first component.

16. The feedthrough system according to claim 11, wherein the electrical contact element has the three dimensional form of a hollow body, preferably the form of a blind hole or a through hole, and optionally wherein the hollow body comprises on its inner surface a fixing element.

17. The feedthrough system according to claim 11, wherein the electrical contact element has a height of in the range of from 10 µm to 5 mm, and optionally wherein the electrical contact element has a width in the range of from 10 µm to 10 mm.

18. The feedthrough system according to claim 11, wherein the electrically conductive pad is a cermet pad.

19. The feedthrough system according to claim 11, wherein the electrically conductive pad has a first component being a cermet pad and a second component being a metal pad, wherein the first component is attached to the electrically conductive pathway, and wherein at least the second component is attached to the electrical contact element.

20. The feedthrough system according to claim 11, wherein the electrical contact element is suitable for connecting a wire to the electrically conductive pathway of the feedthrough by brazing, soldering or melting the wire to the contact element.

* * * * *